US012558254B2

(12) United States Patent
Czaplewski et al.

(10) Patent No.: US 12,558,254 B2
(45) Date of Patent: Feb. 24, 2026

(54) OSTOMY APPLIANCE AND CLEANABLE FILTER ASSEMBLY

(71) Applicant: Hollister Incorporated, Libertyville, IL (US)

(72) Inventors: Gregory J. Czaplewski, Bloomingdale, IL (US); Brian T. Leadingham, Pleasant Prairie, WI (US); Patrick C. Tetzlaff, Caledonia, WI (US)

(73) Assignee: HOLLISTER INCORPORATED, Libertyville, IL (US)

( * ) Notice: Subject to any disclaimer, the term of this patent is extended or adjusted under 35 U.S.C. 154(b) by 425 days.

(21) Appl. No.: 17/800,116

(22) PCT Filed: Jan. 20, 2021

(86) PCT No.: PCT/US2021/014148
§ 371 (c)(1),
(2) Date: Aug. 16, 2022

(87) PCT Pub. No.: WO2021/178058
PCT Pub. Date: Sep. 10, 2021

(65) Prior Publication Data
US 2023/0070877 A1     Mar. 9, 2023

Related U.S. Application Data

(60) Provisional application No. 62/985,090, filed on Mar. 4, 2020.

(51) Int. Cl.
*A61F 5/445* (2006.01)
*A61F 5/441* (2006.01)
(52) U.S. Cl.
CPC .............. *A61F 5/445* (2013.01); *A61F 5/441* (2013.01)

(58) Field of Classification Search
CPC ................... A61F 5/4405; A61F 5/441; A61F 2005/4415; A61F 5/445
See application file for complete search history.

(56) References Cited

U.S. PATENT DOCUMENTS 2,524,750 A * 10/1950 Bellinger ................ A61F 5/445
604/355
4,938,749 A * 7/1990 Jensen .................... A61F 5/441
55/385.4

(Continued)

FOREIGN PATENT DOCUMENTS

EP        2628471 A1 *  8/2013  ............. A61F 5/441
GB        2177301 A  *  1/1987  ............. A61F 5/441
(Continued)

OTHER PUBLICATIONS

International Preliminary Report on Patentability issued by ISA/EPO in connection with PCT/US2021/014148 on Sep. 6, 2022.
(Continued)

*Primary Examiner* — Adam Marcetich
*Assistant Examiner* — Ted Yang
(74) *Attorney, Agent, or Firm* — Klintworth & Rozenblat LLP

(57) ABSTRACT
An ostomy appliance (10) includes a pouch wall (12) defining at least a portion of a collection chamber (14) configured to collect and store effluent from a stoma, an inlet (20) formed in the pouch wall configured to be positioned adjacent to the stoma, and a filter assembly (110) connected to the pouch wall. The filter assembly includes a base (112), a carrier (114), and at least one filter (116). The base includes a vent opening (118) disposed in fluid communication with the collection chamber, the carrier is movably connected to the base, and the at least one filter retained in the carrier. The carrier is operable to move the at least one filter relative to the vent opening to clean the filter by way of contact
(Continued)

between the base and filter during movement of the filter relative to the base. An stomy appliance including a slidable filter assembly for cleaning a filter is also provided.

21 Claims, 10 Drawing Sheets

(56)                    References Cited

U.S. PATENT DOCUMENTS

| | | | | |
|---|---|---|---|---|
| 5,690,621 | A | * | 11/1997 | Canela ................. A61F 5/4407 |
| | | | | 604/333 |
| 6,241,712 | B1 | * | 6/2001 | Steer ....................... A61F 5/441 |
| | | | | 604/333 |
| 2006/0271002 | A1 | * | 11/2006 | Botten .................... A61F 5/441 |
| | | | | 604/339 |
| 2010/0174255 | A1 | * | 7/2010 | Axelsson ................ A61F 5/448 |
| | | | | 604/338 |
| 2017/0209294 | A1 | * | 7/2017 | Apolinario ............. A61F 5/441 |

FOREIGN PATENT DOCUMENTS

| | | | | | |
|---|---|---|---|---|---|
| GB | | 2270265 | A | * | 3/1994 ............. A61F 5/441 |
| GB | | 2329338 | A | * | 3/1999 ............. A61F 5/441 |
| WO | | 03071997 | A1 | | 9/2003 |
| WO | WO-2006048019 | | A1 | * | 5/2006 ............. A61F 5/441 |

OTHER PUBLICATIONS

International Search Report issued by ISA/EPO in connection with PCT/US2021/014148 on Apr. 15, 2021.
Written Opinion issued by ISA/EPO in connection with PCT/US2021/014148 on Apr. 15, 2021.
European Office Action issued in connection with EP application No. 21705056.6 dated Jan. 31, 2025, 6 pages.

* cited by examiner

OSTOMY APPLIANCE AND CLEANABLE FILTER ASSEMBLY

This is a National Stage Application of International Patent Application No. PCT/US2021/014148 filed Jan. 20, 2021, which claims the benefit of and priority to U.S. Provisional Application No. 62/985,090 filed Mar. 4, 2020, the entirety of which are incorporated fully herein by reference.

BACKGROUND

The following description relates to an ostomy appliance, for example, an ostomy pouch having a filter assembly with a cleanable filter.

A known ostomy bag is configured to collect and store effluent discharged from a stoma. As effluent collects within the ostomy bag, a gas within the bag is displaced which may cause an increase in pressure. To relieve this pressure, a known ostomy bag may include a filter disposed in a wall of the ostomy bag which allows the gas to vent from the bag. The filter may be configured to deodorize the gas as the gas is vented to the atmosphere.

However, the filter may become partially or completely occluded, for example, by effluent within the bag. An occluded filter may restrict venting of the gas through the filter. In such circumstances, pressure may accumulate in the bag, which may lead to undesirable ballooning of the bag.

Accordingly, it is desirable to provide an ostomy appliance, such as an ostomy pouch, having a filter assembly with a filter which may be cleaned or refreshed in the event the filter becomes occluded.

SUMMARY

According to one aspect, an ostomy appliance includes a pouch wall defining at least a portion of a collection chamber configured to collect and store effluent from a stoma, an inlet formed in the pouch wall configured to be positioned adjacent to the stoma, and a filter assembly connected to the pouch wall. The filter assembly includes a base, a carrier and a filter. The base has a vent opening disposed in fluid communication with the collection chamber. The carrier is movably connected to the base. The filter is retained in the carrier. The carrier is operable to move the at least one filter relative to the vent opening to clean or refresh the filter.

The filter may be disposed in sliding contact with the base during movement of the filter relative to the vent opening. The filter may include a first portion extending across the vent opening and a second portion adjacent to the vent opening. Movement of the filter relative to the vent opening in a first direction may cause the first portion to move away from the vent opening and the second portion to move so that it extends across the vent opening. Movement of the second portion to extend across the vent opening may refresh the filter. Movement of the filter relative to the vent opening in a second direction opposite to the first direction may cause the first portion to move to a position extending across the vent opening and the second portion to move away from the vent opening.

The carrier may include a receptacle and the filter may be retained in the receptacle. The carrier may include two receptacles and the filter may include first and second filter elements retained in respective receptacles. The filter may be disposed between the carrier and the base. The carrier may include a plurality of atmosphere vent openings for venting gas from the collection chamber to the atmosphere. The filter may include a hydrophobic membrane.

In an embodiment, the carrier may be slidably connected to the base and the carrier and the filter may be configured for linear sliding movement relative to the base. The base may include a plate and a flange extending from the plate. The carrier may be connected to the flange for sliding movement. In another embodiment, the carrier may be rotatably connected to the base and the carrier and the filter may be configured for rotational movement relative to the base.

Movement of the filter relative to the base may clean the filter by bringing accumulated effluent on the filter into contact with the base to remove the accumulated effluent from the filter. The base may include a vent wall around the vent opening, and accumulated effluent may be removed from the filter by the vent wall as the filter moves relative to the vent wall. In an embodiment, the base may include a raised lip. Accumulated effluent may be removed from the filter by the raised lip as the filter moves relative to the raised lip.

In an embodiment, the base may include a raised lip, and the filter may be disposed in sliding contact with the raised lip. The filter may be removably retained in the carrier.

According to another aspect, an ostomy appliance includes a pouch wall defining at least a portion of a collection chamber configured to collect and store effluent from a stoma, an inlet formed in the pouch wall configured to be positioned adjacent to the stoma, and a slidable filter assembly connected to the pouch wall. The slidable filter assembly includes a base, a carrier retained on and slidable relative to the base, and a filter in slidable contact with the base and movable with the carrier relative to the base. The base includes a vent opening disposed in fluid communication with the collection chamber. The carrier is operable to slide the at least one filter relative to the vent opening to clean the filter by way of contact between the base and the filter during sliding movement of the filter.

In one embodiment, the carrier and the filter may be linearly slidable relative to the base. In another embodiment, the carrier and the filter may be rotationally slidable relative to the base. The base may further include a raised lip and the filter may be disposed in sliding contact with the raised lip.

Other objects, features, and advantages of the disclosure will be apparent from the following description, taken in conjunction with the accompanying sheets of drawings, wherein like numerals refer to like parts, elements, components, steps, and processes.

DETAILED DESCRIPTION

Figure 1:
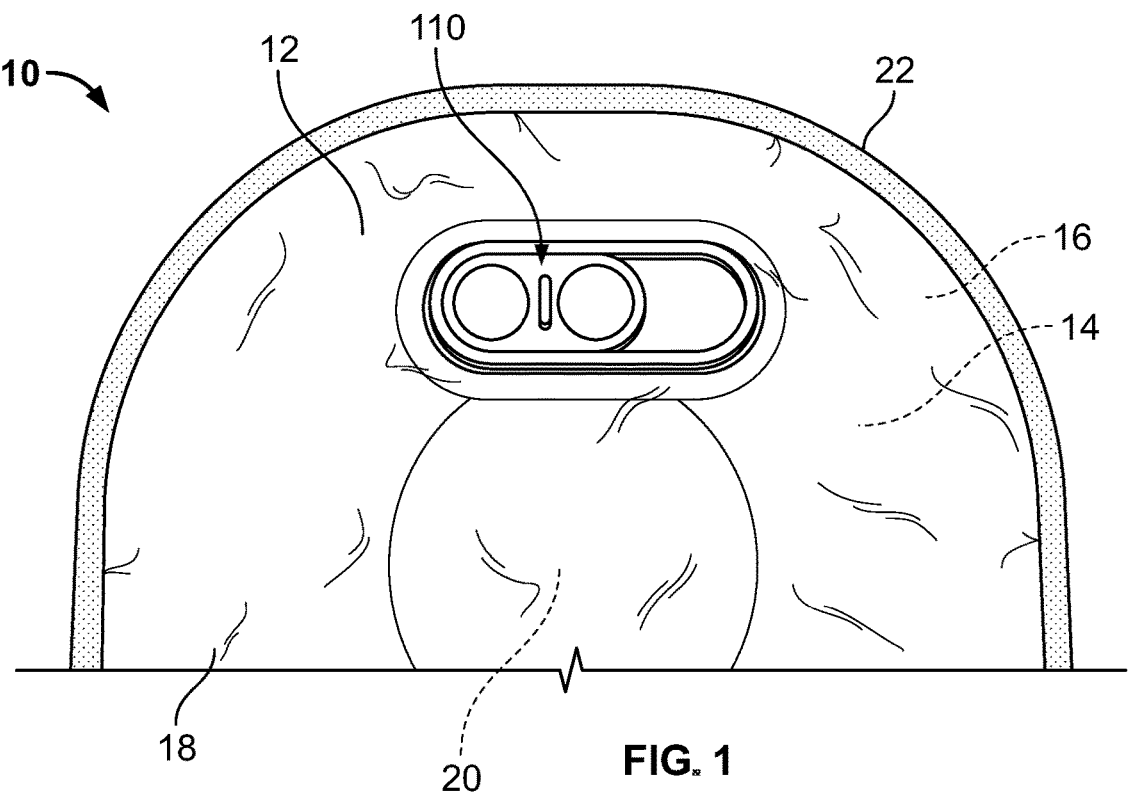
FIG. 1 is a plan view showing a portion of an ostomy appliance having a cleanable filter assembly according to an embodiment.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

Figure 2:
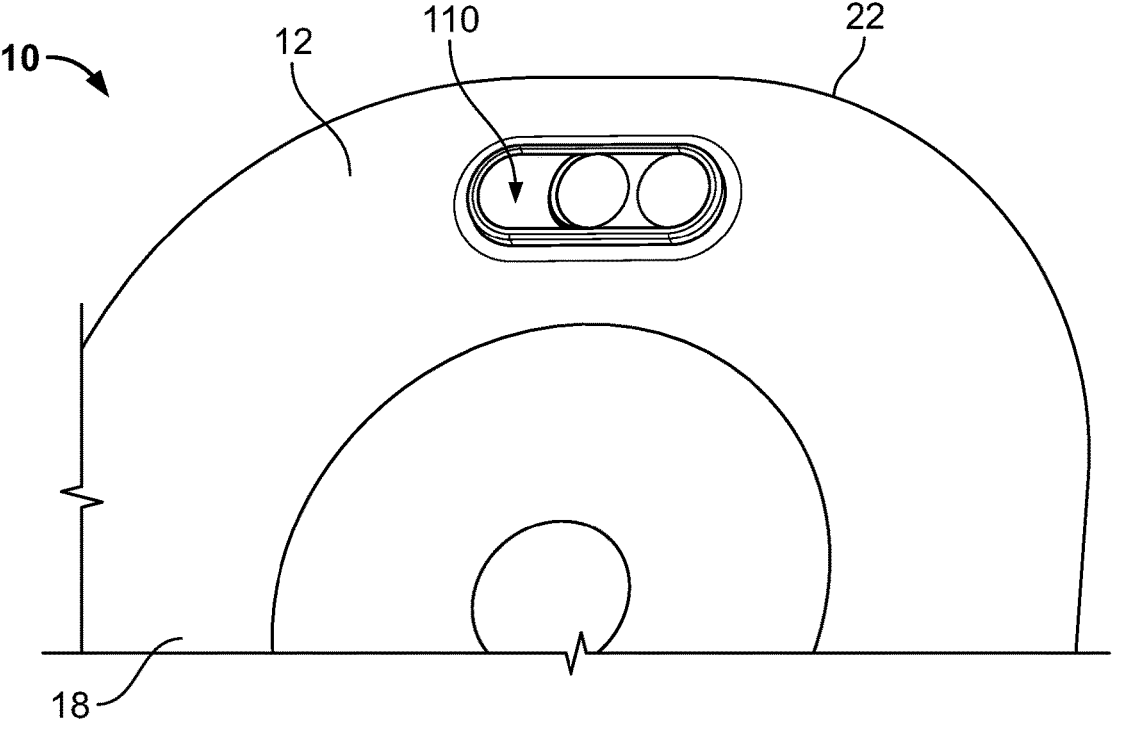
FIG. 2 is another plan view showing a portion of an ostomy appliance having a cleanable filter assembly according to an embodiment.

FIGS. 1 and 2 are plan views showing a portion of an ostomy appliance 10 having a cleanable filter assembly 110, according to an embodiment. The ostomy appliance 10 may be an ostomy pouch configured to be secured to a user in a known manner. In one embodiment, the ostomy appliance 10 may include a pouch wall 12 defining at least a portion of a collection chamber 14 within the ostomy appliance 10. The collection chamber 14 may be configured to receive and store effluent discharged from a stoma. The pouch wall 12 may include a proximal sidewall 16 configured to face a user's body and a distal sidewall 18 configured to face away from the user's body. The collection chamber 14 may be formed between the proximal sidewall 16 and the distal sidewall 18. A stoma inlet opening 20 may be formed in the proximal sidewall 16 and may be configured to fit around the stoma when the ostomy appliance 10 is secured to the user. In one embodiment, the proximal sidewall 16 and the distal sidewall 18 may be separately formed and sealed together along their respective peripheries to form an outer periphery 22 of the pouch wall 12.

Figure 3:
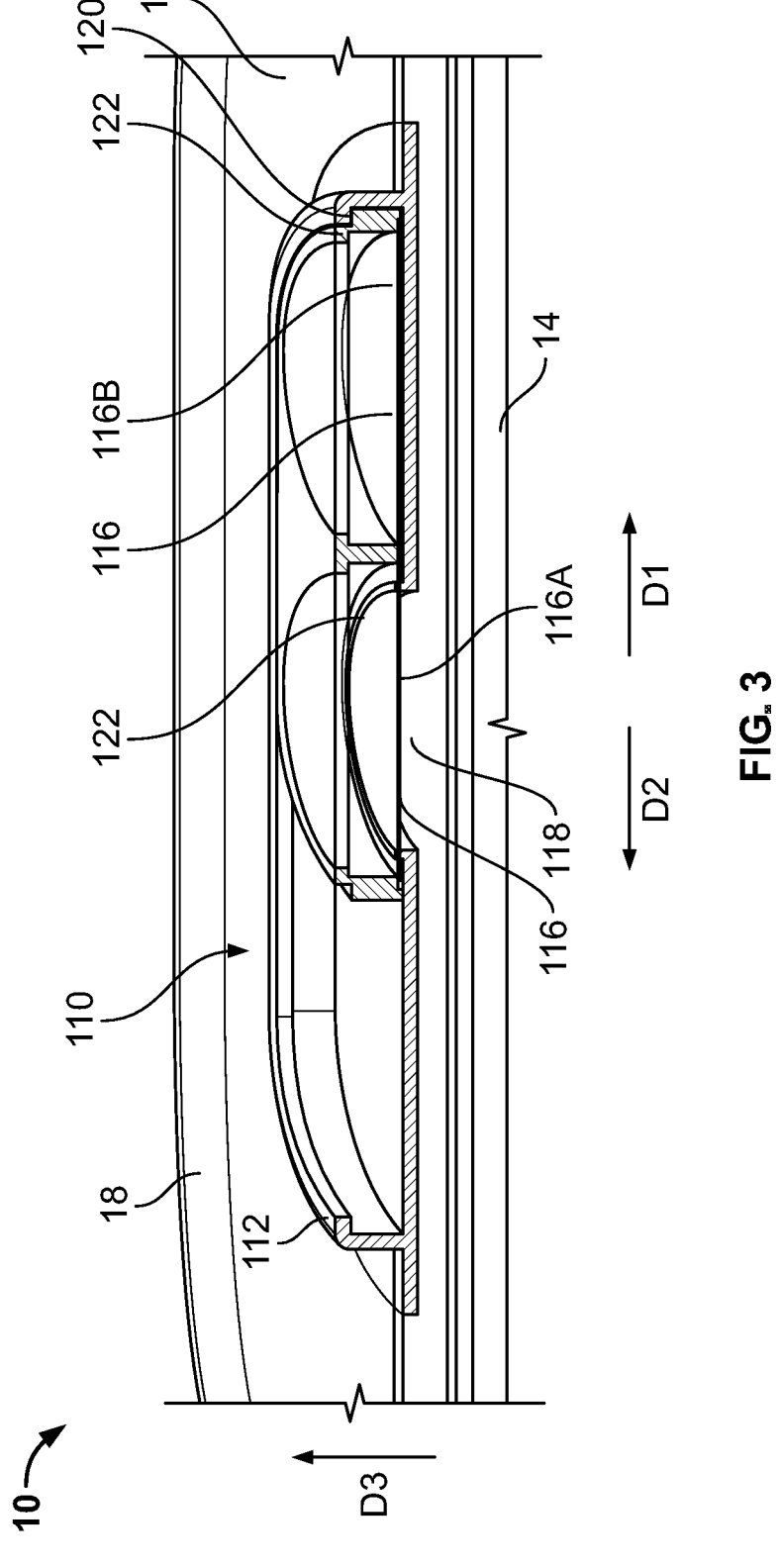
FIG. 3 is a cross-sectional view of a cleanable filter assembly according to an embodiment.

The filter assembly 110 may be connected to the pouch wall 12. In one embodiment, the filter assembly 110 may be connected to the distal sidewall 18 and positioned generally at an upper portion of the ostomy appliance 10, spaced from a portion of the collection chamber 14 where effluent is typically stored. In one embodiment, the filter assembly 110 may include a base 112, a carrier 114 and a filter 116 (FIG. 3). Gas may be vented from the collection chamber 14 to the atmosphere through the filter 116. The filter 116 may be a single filter element or include a plurality of filter elements.

For example, in embodiment, the filter 116 may include a first filter element 116A and a second filter element 116B (FIG. 3)

In one embodiment, the filter 116 may be a porous, gas-permeable filter configured to deodorize a gas flowing through the filter 116. Examples of such filters include known carbon filters, including charcoal filters, commonly used in ostomy appliances. The filter 116 may include a hydrophobic membrane so that the filter 116 is substantially liquid impermeable. The hydrophobic membrane may be formed, for example, on a side of the filter 116 facing the collection chamber 14 and on a side of the filter 116 facing the atmosphere.

FIG. 3 is a cross-sectional view of the filter assembly 110 according to an embodiment. The base 112 may be secured to the pouch wall 12 using a suitable, known fastening technique, such as heat sealing, welding, adhesive bonding, or the like. The base 112 includes a vent opening 118 configured to be disposed in fluid communication with the collection chamber 14. The carrier 114 may be connected to the base 112 by a fastening arrangement 120. The fastening arrangement 120 is configured to allow movement of the carrier 114 relative to the base 112 in at least one direction and substantially prevent or limit inadvertent or unintentional removal of the carrier 114 from the base 112. The fastening arrangement 120 may be a known arrangement including, but not limited to, one or more known fasteners suitable for permitting relative movement between adjacent, fastened parts in at least one direction. For example, in one embodiment, the fastening arrangement 120 may allow for sliding movement of the carrier 114 relative to the base 112 in one or more of a first sliding direction D1 and a second sliding direction D2 opposite to the first sliding direction D1. The sliding movement may be a linear sliding movement. The fastening arrangement 120 may also prevent or limit inadvertent or unintentional movement of the carrier 114 relative to the base 112, for example in a third direction D3, which may extend at a non-parallel angle relative to the first sliding direction D1 and the second sliding direction D2. In this manner, the carrier 114 may be held against inadvertent removal from the base 112 and/or a substantially sealed gas vent path may be maintained through the filter assembly 110.

The carrier 114 is configured to retain the filter 116 such that the filter 116 is movable with the carrier 114 relative to the base 112. That is, the carrier 114 may be operable to move the filter 116 relative to the base 112. In one embodiment, the carrier 114 may include one or more receptacles 122 for retaining the filter 116. For example, the filter 116 may be embedded in the one or more receptacles 122. In an embodiment, the one or more receptacles 122 may retain respective filter elements 116A, 116B. The present disclosure is not limited to such one or more receptacles 122, however, and other techniques for retaining the filter 116 are envisioned, including, but not limited to, one or more known suitable fasteners.

Figures 4, 5:
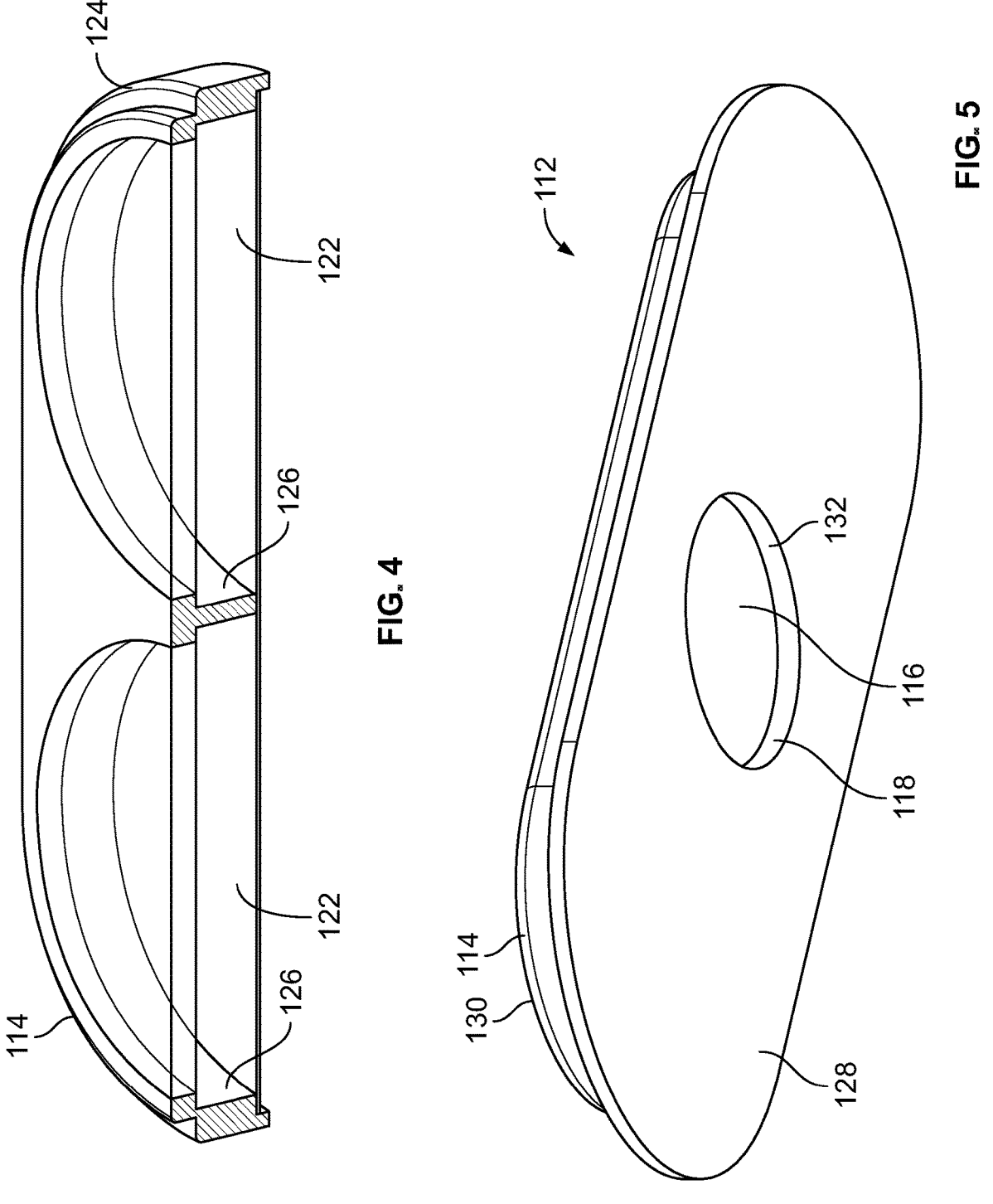
FIG. 4 is a perspective cross-sectional view showing a carrier of the filter assembly of FIG. 3 according to an embodiment.
FIG. 5 is a perspective view showing a base of the filter assembly of FIG. 3 according to an embodiment.

FIG. 4 is a perspective cross-sectional view of the carrier 114, according to an embodiment. In one embodiment, the carrier 114 may include a first part 124 of the fastening arrangement 120. In one embodiment, the first part 124 may be, for example, a shoulder, tab or other similar projection. In one embodiment, the one or more receptacles 122 may include two receptacles 122. The receptacle(s) 122 may include an inner wall 126. Movement of the carrier 114 in a predetermined direction relative to the base 112 may cause the inner wall 126 to push the filter 116 disposed at least partially within the receptacle 122 such that the filter 116 moves with the carrier 114.

FIG. 5 is a perspective view showing a side of the base 112 configured for facing the collection chamber 14, according to an embodiment. In one embodiment, the base 112 includes a plate 128 and a flange 130 extending from the plate 128. The vent opening 118 may be defined, at least partially, by a vent wall 132. Accordingly, the vent opening 118 may extend through the entire thickness of the plate 128. In use, the filter 116 may extend across the vent opening 118, such that gas may flow from the collection chamber 14 into the filter 116 through the vent opening 118.

Figures 6, 7:
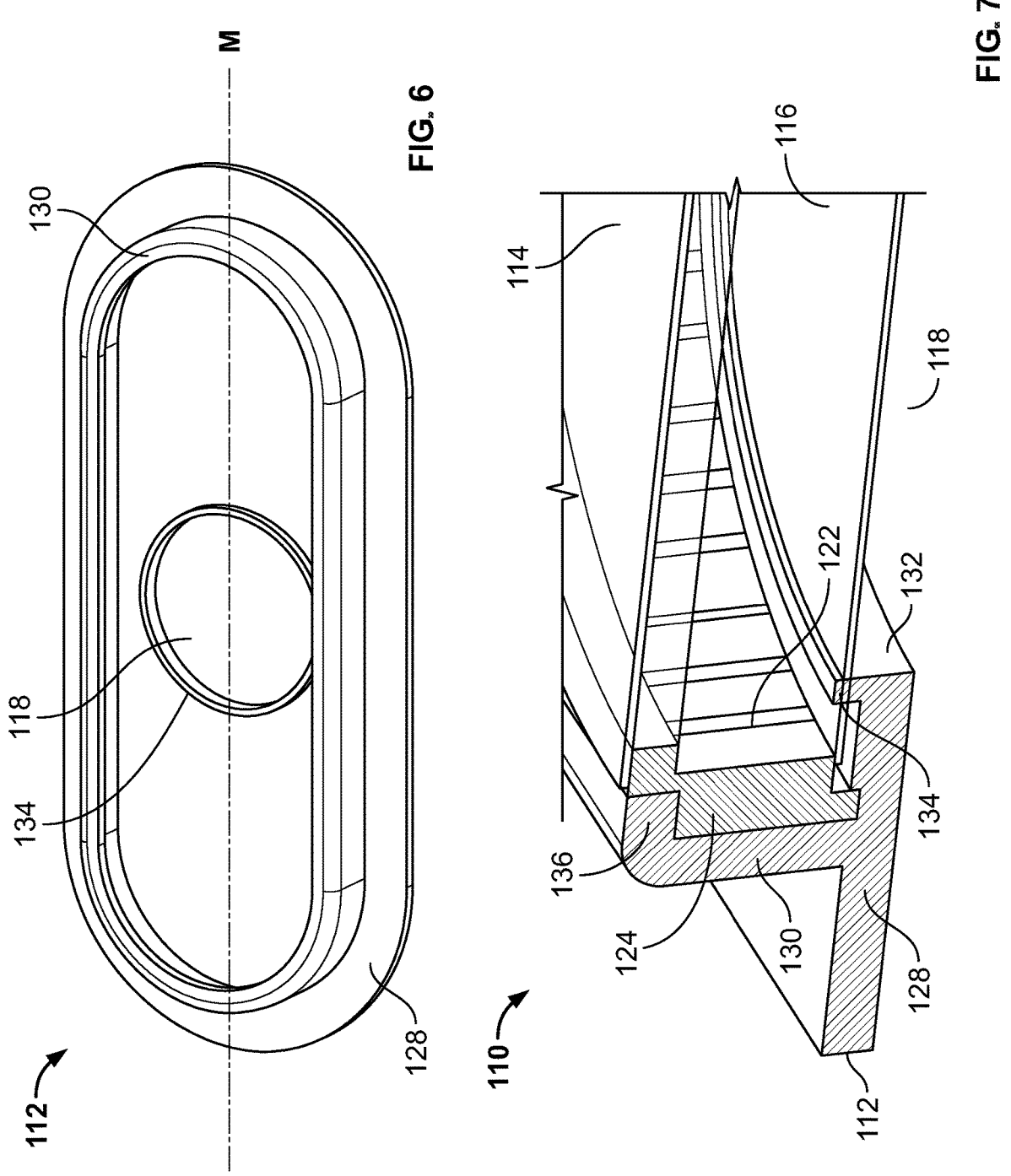
FIG. 6 is another perspective view showing the base of FIG. 5.
FIG. 7 is an enlarged perspective view showing a cross-section of a portion of the cleanable filter assembly of FIG. 3 according to an embodiment.

FIG. 6 is a perspective view showing a side of the base 112 configured to face away from the collection chamber 14, i.e., toward the atmosphere, according to an embodiment. In one embodiment, the flange 130 may define at least a portion of a path of movement for the carrier 114. In one embodiment, the flange 130 may be a closed loop having an elongated shape. The carrier 114 may slide relative to the base 112, for example, along a major axis 'M' of the closed loop. The base 112 may optionally include a raised lip 134 at least partially surrounding, or disposed adjacent to, the vent opening 118. The raised lip 134 may project outwardly from the plate 128. The raised lip 134 may contact at least a portion of the filter 116 facing the collection chamber 14. In one embodiment, the raised lip 134 may be flush with the vent wall 132.

FIG. 7 is an enlarged perspective view showing a cross-section of a portion of the filter assembly 110 according to an embodiment. In one embodiment, a second part 136 of the fastening arrangement 120 may be formed on the flange 130 of the base 112. The second part 136 may be, for example, a projection, tab or the like configured to engage the first part 124 of the fastening arrangement 120. In one embodiment, the base 112 may be made of a flexible, resilient material, including known moldable materials, such that the carrier 114 may be connected to the flange 130 via a snap fit between the first part 124 and the second part 136.

Referring generally to FIGS. 1-7, according to embodiments, a filter 116 may be retained by the carrier 114, for example, by positioning the filter 116 in a receptacle 122 of the carrier 114. The filter 116 may be retained in the receptacle 122, for example, by friction fit and/or with a suitable fastener. The carrier 114 may be movably connected to the base 112 by the fastening arrangement 120 and configured for sliding movement relative to the base 112. In one embodiment, the carrier 114 may be configured for movement along a path at least partially defined by the flange 130 of the base 112. In use, the carrier 114 may be positioned so that the filter 116 is disposed over the vent opening 118 for gas venting and filter functionality, for example, when a user is wearing the appliance. Accordingly, gas may be vented from the collection chamber 14 through the vent opening 118 and the filter 116 to the atmosphere. The gas may be deodorized as it passes through the filter 116.

In some instances, effluent in the collection chamber 14 may accumulate on the filter 116, for example, on the hydrophobic membrane of the filter 116, in the region of the vent opening 118. Such accumulation may occlude the filter 116 and restrict gas venting through the filter 116. According to the embodiments described above and shown in FIGS. 1-7, the carrier 114 and the filter 116, while secured to the base 112, may be moved relative to the vent opening 118 to clean and/or refresh the filter 116. In this manner, the accumulation of effluent on the filter 116 in or near the vent opening 118 may be removed from the vent opening to improve gas venting.

For example, the carrier 114 and the filter 116 may be moved in a predetermined direction, such as the second sliding direction D2 shown in FIG. 3. In an embodiment, the effluent accumulated on the filter 116, and/or the hydrophobic membrane, may move with the filter 116 in the second sliding direction D2, and be brought into contact with a portion of the base 112. For instance, as the filter 116 moves away from the vent opening 118, the accumulated effluent may be brought into contact with the vent wall 132 and/or the raised lip 134. Continued movement of the filter 116 in the same direction may cause the accumulated effluent to be removed from the filter 116 by way of contact between the base 112 and the effluent. For example, the effluent may be scraped from the filter 116 by the vent wall 132 and/or the raised lip 134. In an embodiment, the filter 116 may be moved in the predetermined direction, for example, the first and/or second sliding direction D1, D2, a distance that is equal to or greater than a width of the vent opening 118 in the first and/or second sliding direction D1, D2, such that a portion of filter 116 exposed to effluent through the vent opening 118 may be moved completely away from the vent opening 118. Accordingly, the filter 116 may be cleaned by removing accumulated effluent from the filter 116.

In one embodiment, the filter 116 may be moved in the predetermined direction, such as the second sliding direction D2, a distance sufficient to dispose the filter 116 substantially adjacent to the vent opening 118. The filter 116 may then be moved in an opposite direction, such as the first sliding direction D1, and returned to a position where the filter 116 extends across the vent opening 118 for gas venting. In this manner, accumulated effluent may be removed from the filter 116 by moving the filter relative to the base 112 in one direction, and the cleaned filter 116 (i.e., the filter 116 after removal of the accumulated effluent) may be returned to a position for venting and filtering gas from the collection chamber 14.

Alternatively, or in addition, the filter 116 may be sized to have a first portion extending across the vent opening 118 and a second portion adjacent to the vent opening 118. In such an embodiment, gas may be vented from the collection chamber 14 through the first portion of the filter 116 when the first portion extends across the vent opening. The filter 116 may be moved in a predetermined direction, as described above, such that the first portion is moved away from the vent opening 118 and the second portion is moved to extend across the vent opening 118. Gas may be vented from the collection chamber 14 through the second portion of the filter 116 when the second portion extends across the vent opening 118.

In one embodiment, accumulated effluent may be removed from the first portion of the filter 116 in the manner described above, to clean the filter 116. Alternatively, or in addition, movement of an occluded portion of the filter 116, for example, the first portion, from a position extending across the vent opening 118 to a position adjacent to the vent opening, along with movement of a second, clean (i.e., non-occluded) portion of the filter 116 to extend across the vent opening 118, may refresh the filter 116, for gas venting through the second portion. Thus, in some embodiments, movement of the filter 116 may move an occluded portion of the filter 116 out of a gas venting path and move a clean portion of the filter 116 into the gas venting path, i.e., extending across the vent opening 118, to refresh the filter 116.

In embodiments, the filter assembly 110 may be configured to remove effluent the filter 116 by minimizing or eliminating a clearance between the filter 116 and the base 112 at least during movement of the filter 116 relative to the base 112. For example, in an embodiment, the filter 116 may be positioned having a relatively low clearance from the base 112. The clearance may remain substantially constant during movement of the filter 116 relative to the base 112. In some embodiments, at least a portion of the filter 116 may be disposed in contact with at least a portion of the base 112. For example, the filter 116 may be disposed in sliding contact with a portion of the base 112 immediately adjacent the vent wall 132, and/or in sliding contact with the raised lip 134. The filter 116 may remain in sliding contact with the base 112 during movement of the filter 116 relative to the base 112 to clean or refresh the filter 116. In one embodiment, accumulated effluent may be removed from the filter 116 by way of being moved into contact with a portion of the base 112 which contacts the filter 116. That is, a portion of the base 112, such as the vent wall 132 or raised lip 134 may act as a wiper to remove effluent from the filter 116. Alternatively, in some embodiments, sufficient clearance may be provided between the filter 116 and the base at least during movement of the filter 116 relative to the base 112 such that effluent moves with the filter 116 to a position adjacent the vent opening 118.

In one embodiment, the first portion may be the first filter element 116A and the second portion may be the second filter element 116B. The first and second filter elements 116A, 116B may be separate, discrete filter elements. Alternatively, the first and second filter elements 116A, 116B may be separate portions of a single, continuous filter 116.

In one embodiment, the raised lip 134 may be provided to assist in removal of accumulated effluent from the filter 116 as the filter 116 is moved relative to the vent opening 118. The raised lip 134 may be angled to form a peak which may provide a relatively small cross section in contact with the filter 116 (or hydrophobic membrane), while still allowing sliding movement of the filter 116 relative to the raised lip 134 in an intended manner to remove, clean or scrape effluent from the filter 116. In other embodiments, the raised lip 134 may be, for example, substantially curved, rounded, flat, or stepped, or combinations thereof, in cross-section.

In one embodiment, the carrier 114 may be moved to a closed position, such that gas venting from the collection chamber 14 through the filter assembly 110 is substantially prevented. In such an embodiment, the carrier 114 may include a substantially gas impermeable surface adjacent to the filter 116. The carrier 114 may be moved from a position in which the filter 116 is disposed over the vent opening 118 for gas venting to a position in which the substantially gas impermeable surface is disposed over the vent opening 118 to limit or prevent gas venting.

FIGS. 8-17 show examples of the ostomy appliance 10 having a cleanable filter assembly 210 according to another embodiment. Where certain features described below are the same or substantially the same as those described above, like terminology and/or reference numbers may be used, additional description may be omitted, and/or additional description may be limited to any differences between the embodiments.

Figure 8:
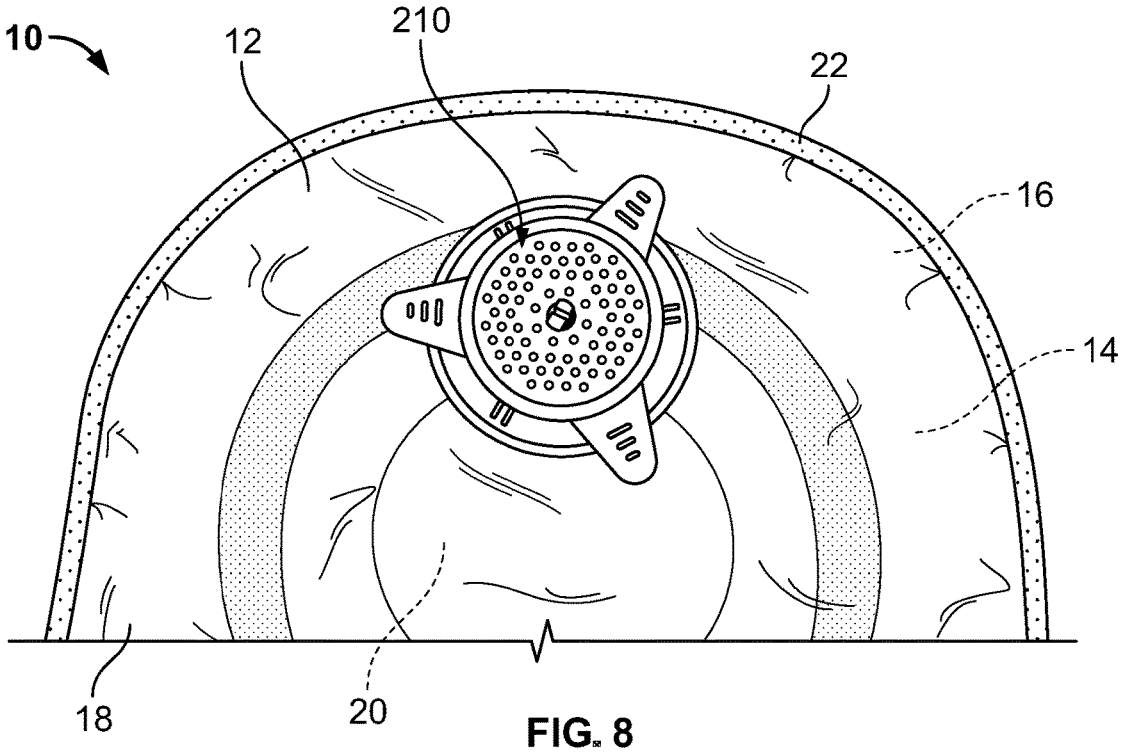
FIG. 8 is a plan view showing a portion of an ostomy appliance having a cleanable filter assembly according to another embodiment.

FIG. 8 is a plan view showing a portion of the ostomy appliance 10 having a cleanable filter assembly 210 according to another embodiment. The filter assembly 210 may be connected to the pouch wall 12 of the ostomy appliance 10 in a manner similar to the filter assembly 110 described above.

Figure 9:
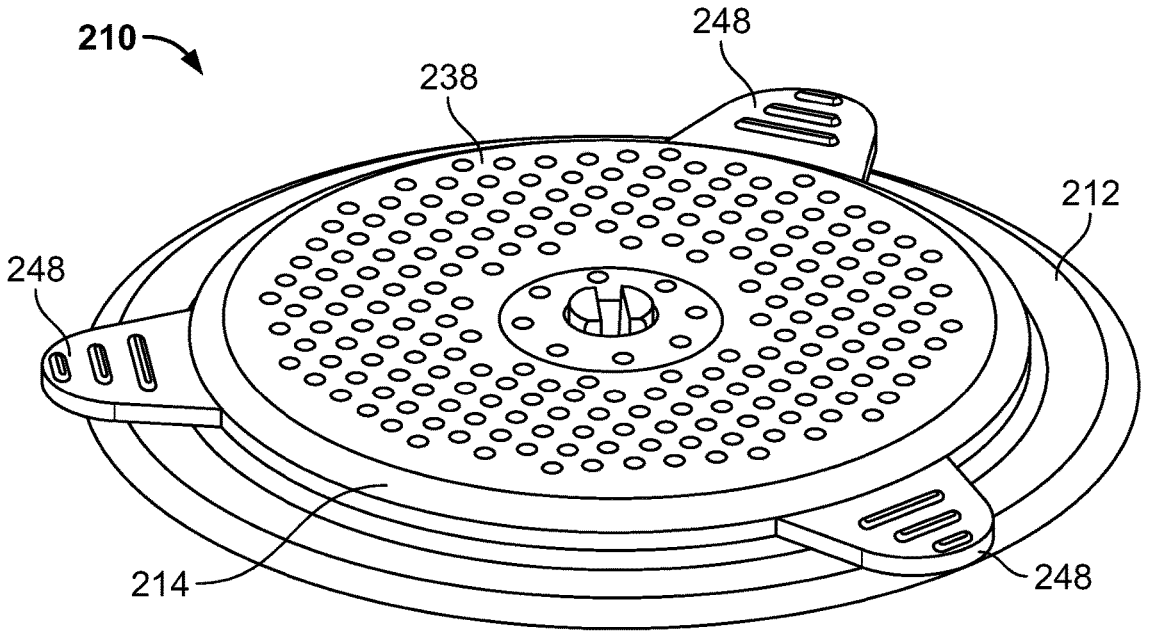
FIG. 9 is a perspective view of the cleanable filter assembly of FIG. 8 according to an embodiment.
Figure 10:
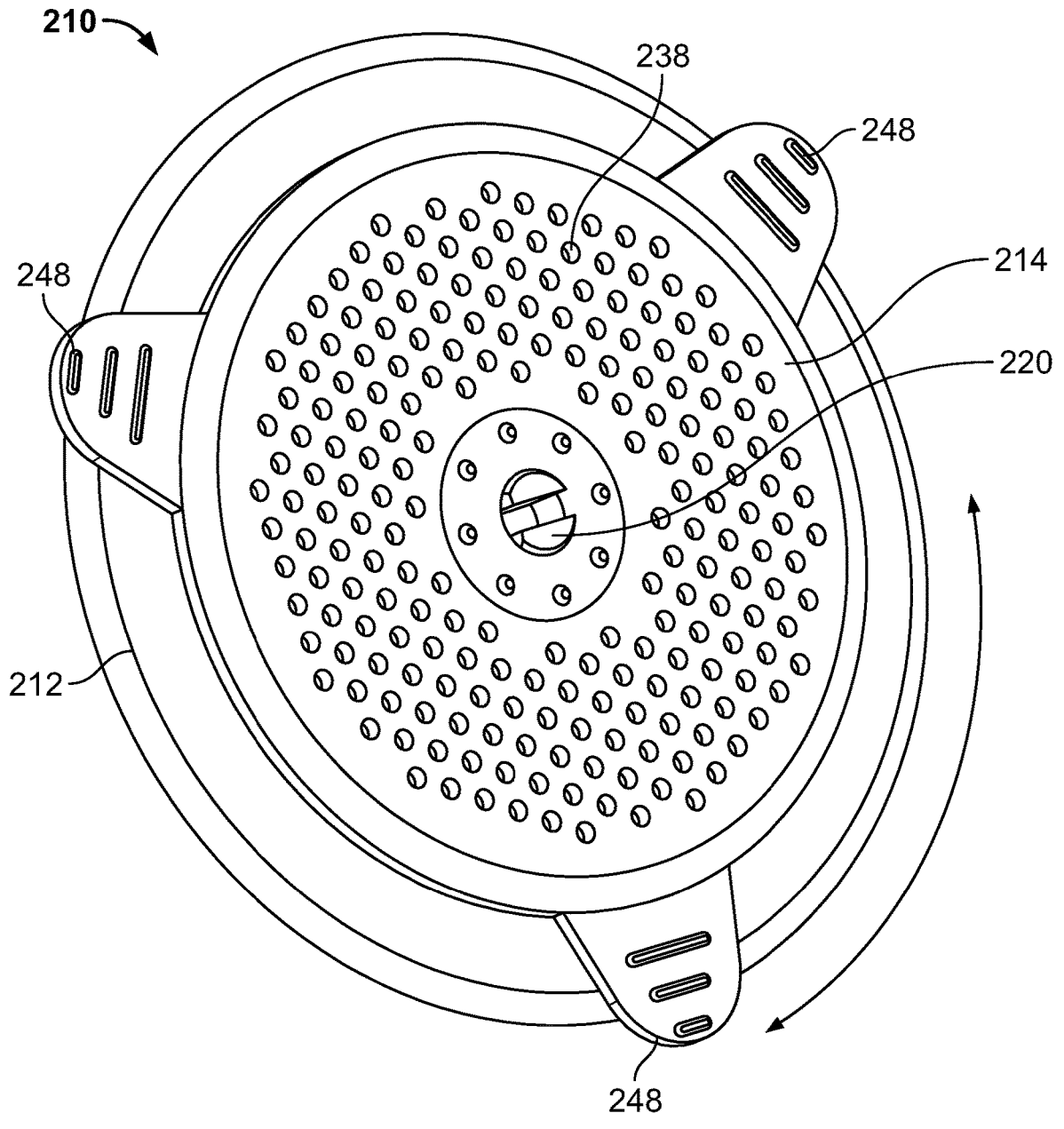
FIG. 10 is another perspective view of the cleanable filter assembly of FIG. 9 according to an embodiment.

FIGS. 9 and 10 are perspective views of the filter assembly 210 according to an embodiment. The filter assembly 210 may include a base 212 and a carrier 214 connected to the base 212 and configured for movement relative to the base 212. In one embodiment, the carrier 214 is configured to rotate relative to the base 212, as indicated with the double arrow in FIG. 10. In one embodiment, the carrier 214 may be positioned coaxially with the base 212. The carrier 214 may also include a plurality of atmosphere vent openings 238. The carrier 214 may further include one or more handling tabs 248.

Figure 11:
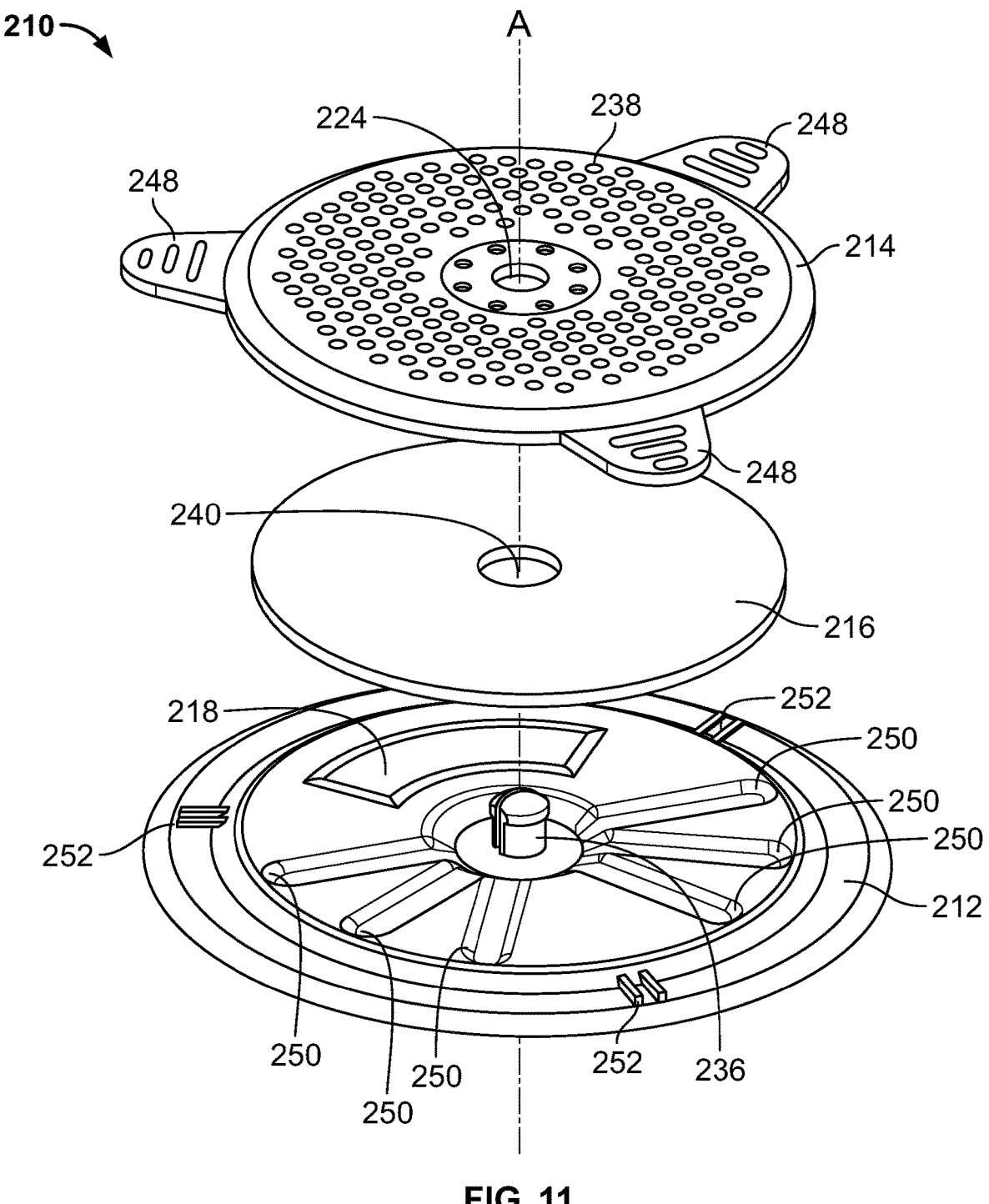
FIG. 11 is an exploded perspective view of the cleanable filter assembly of FIG. 9 according to an embodiment.

FIG. 11 is an exploded view of the filter assembly 210 according to an embodiment. The filter assembly 210 may further include a filter 216 disposed between the base 212 and the carrier 214. In one embodiment, each of the base 212, the carrier 214 and the filter 216 may be substantially disc-shaped. In one embodiment, the filter 216 may be disposed coaxially with the base 212 and the carrier 214. The filter 216 may include a hydrophobic membrane, for example, on a top, carrier-facing surface and a bottom, base-facing surface.

The base 212 may include at least one vent opening 218 configured to be disposed in fluid communication with the collection chamber 14, such that gas from the collection chamber 14 may enter the filter 216 through the vent opening 218. In one embodiment, the vent opening 218 may be spaced from an axis 'A' of the base 212. In one embodiment, the vent opening 218 may be substantially arc-shaped and extend through an angular range. However, other shapes are envisioned for the vent opening 218 as well. In one embodiment, the base 212 may include one or more base channels 250 for promoting airflow adjacent to portions of the filter 216. In one embodiment, the base 212 may include one or more stop detents 252 for indicating a predetermined rotational position of the carrier 214 relative to the base 212. For example, the stop detents 252 may increase rotational resistance when a corresponding portion of the carrier 214 is rotated into contact with a detent 252. Alternatively or in addition, a tactile or audible indication may be provided, such as a bump or click when a corresponding portion of the carrier 214 is rotated into contact with a detent 252.

The filter assembly 210 may include a fastening arrangement 220 for retaining the carrier 214 on the base 212. In one embodiment, the fastening arrangement 220 may include a first part 224 on the carrier 214. The first part 224, in one embodiment, may be an opening, detent or the like. The fastening arrangement 220 may also include a second part 236 on the base 212. In one embodiment, the second part 236 may be a projection, catch or the like. The second part 236 may engage the first part 224, for example, by a friction fit, snap fit or the like. In one embodiment, the fastening arrangement 220 may be a releasable clip, configured to allow the carrier 214 to be selectively connected to and removed from the base 212. Removal of the carrier 214 from the base 212 may allow access to the filter 216, for example, for inspection, manual cleaning and/or replacement of the filter 216.

In one embodiment, the second part 236 may also extend through a filter opening 240 in the filter 216. The first part 224, second part 236, and filter opening 240 may be arranged substantially coaxially on the axis 'A.' The carrier 214 and the filter 216 are configured to rotate relative to the base 212, vent opening 218 and second part 236.

Figure 12:
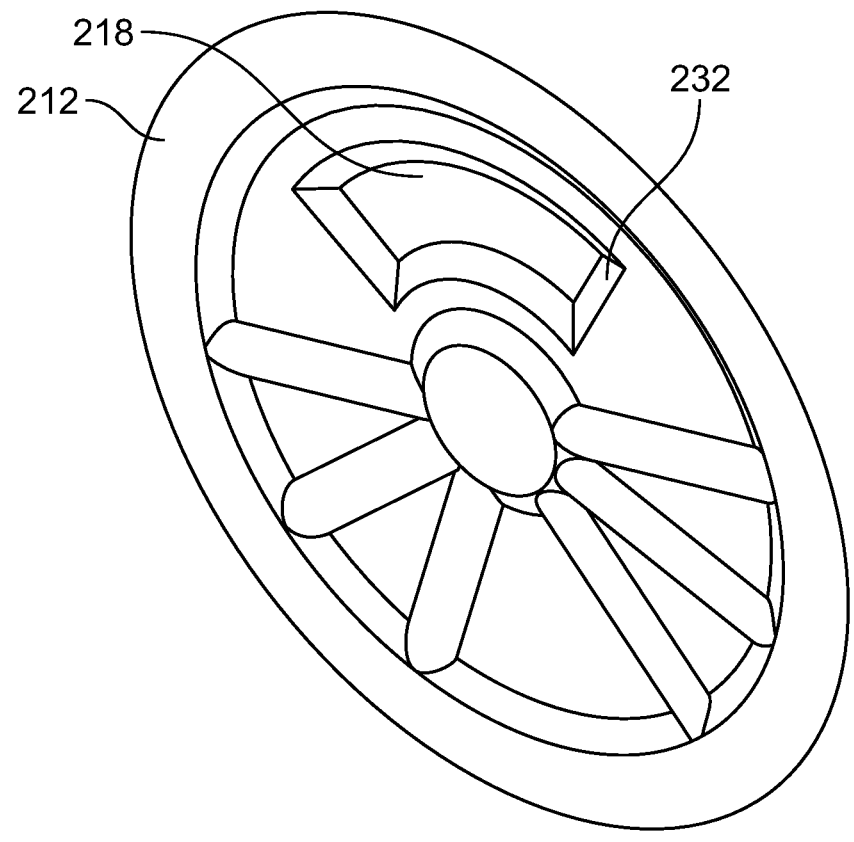
FIG. 12 is a perspective view of a base of the cleanable filter assembly of FIG. 9 according to an embodiment.

FIG. 12 is a perspective view showing a side of the base 212 configured to face the collection chamber 14, according to an embodiment. The vent opening 218 may be surrounded, at least partially, by a vent wall 232 extending through a thickness of the base 212. In some embodiments, the base 212 may include a plurality of vent openings 218.

Figure 13:
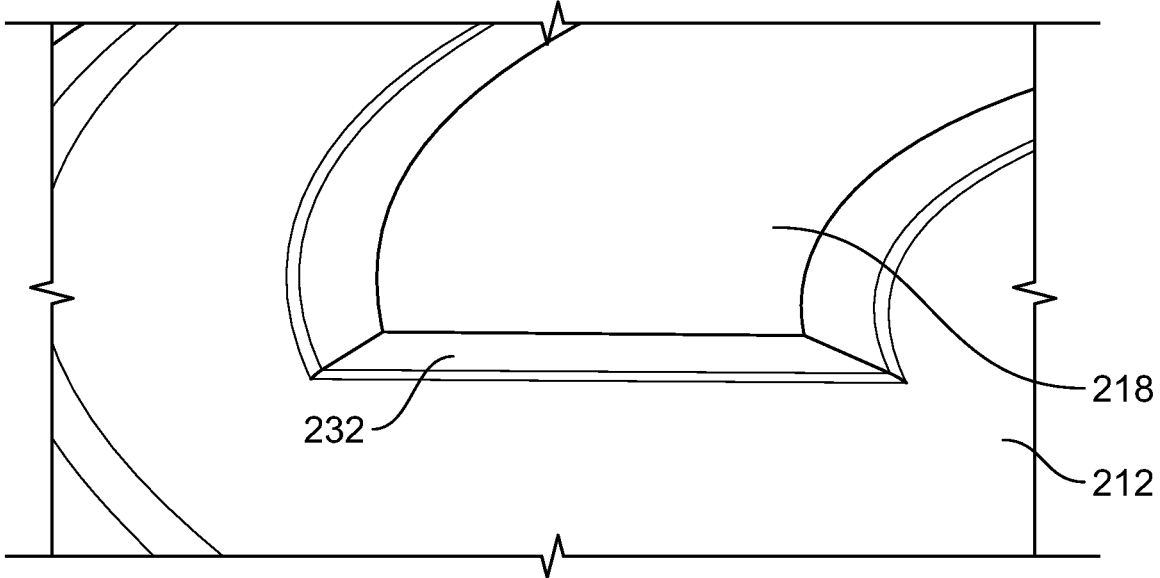
FIG. 13 is an enlarged perspective view showing a portion of the base of FIG. 12 according to an embodiment.

FIG. 13 is an enlarged perspective view of a portion of the base 212 according to an embodiment. In one embodiment, the vent wall 232 may extend through the base 212 in a direction substantially parallel to the axis 'A.' In other embodiments, however, the vent wall 232, or at least one portion of the vent wall 232, may be beveled.

Figures 14, 15:
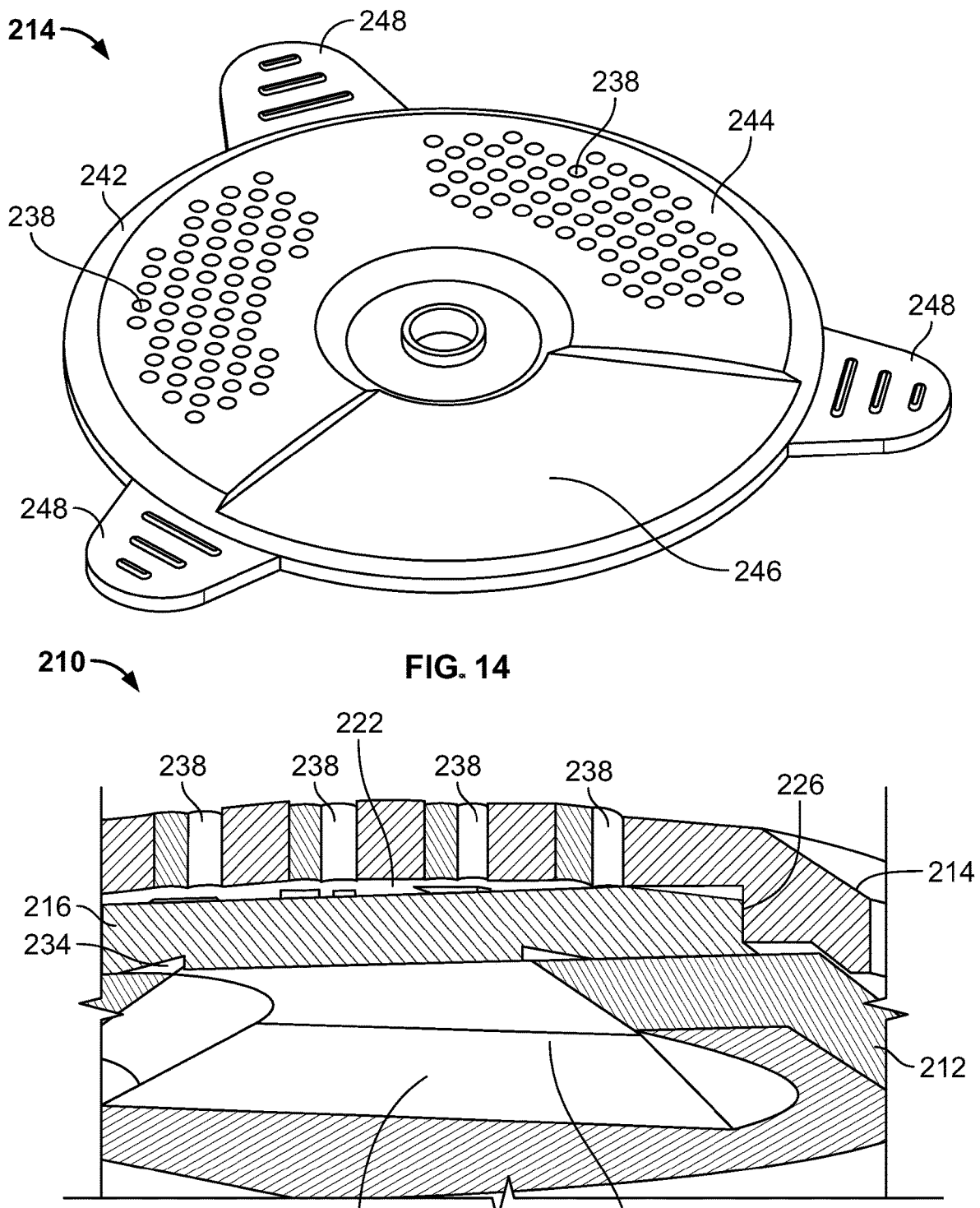
FIG. 14 is a perspective view showing a carrier of the filter assembly of FIG. 9 according to an embodiment.
FIG. 15 is a perspective view showing a cross-section of a portion of the cleanable filter assembly of FIG. 9 according to an embodiment.

FIG. 14 is a perspective view of the carrier 214 according to an embodiment. The plurality of atmosphere vent openings 238 may allow gas to vent from the filter 216 to the atmosphere through the carrier 214. That is, gas vented from the collection chamber 14 and deodorized by the filter 216 may exit to the atmosphere via the atmosphere vent openings 238. In one embodiment, the plurality of atmosphere vent openings 238 may be distributed substantially over an entire angular range (i.e., 360 degrees) of the carrier 214.

In another embodiment, the plurality of atmosphere vent openings 238 may be arranged in one or more angularly spaced sections relative to the axis 'A'. For example, as shown in FIG. 14, the plurality of atmosphere vent openings 238 may be distributed over a first angular section 242 and a second angular section 244. A third angular section 246 of the carrier 214 may be formed without the atmosphere vent openings 238. In such an embodiment, the third angular section 246 may allow for the filter assembly 210 to be placed into a closed or off condition by positioning the third section 246 over the portion of the base 212 in which the vent opening 218 is disposed.

Referring to FIGS. 8-11 and 14, in one embodiment, the one or more handling tabs 248 may project radially outward. In one embodiment, the handling tabs 248 are configured to be gripped or otherwise manipulated by a user to rotate the carrier 214.

FIG. 15 is a perspective view showing a cross-section of a portion of the filter assembly 210 according to an embodiment. One side of the filter 216 (or hydrophobic membrane of the filter 216) may be exposed to the collection chamber 14 through the vent opening 218 and is configured to receive the gas from the collection chamber 14. Gas may flow through the filter 216, where it may be deodorized, and then to the atmosphere through the atmosphere openings 238 of the carrier 214.

Still referring to FIG. 15, in one embodiment, the carrier 214 may have a receptacle 222 configured to receive at least a portion of the filter 216. In one embodiment, the carrier 214 may retain the filter 216 such that the filter 216 is rotatable with the carrier 214. For example, the filter 216 may be retained in the carrier 214 by friction fit or using known, suitable fasteners. Thus, the carrier 214 may be operable to move the filter 216 relative to the base 212. In one embodiment, the carrier 214 includes an inner wall 226 forming at least a portion of the receptacle 222.

Figure 16:
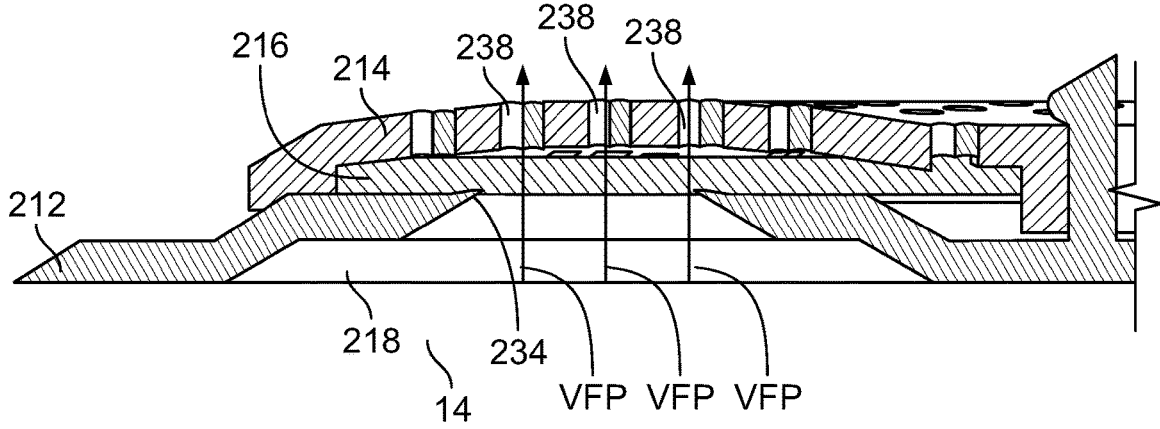
FIG. 16 is a cross-sectional view of a portion of the cleanable filter assembly of FIG. 9 according to an embodiment.

FIG. 16 is another cross-sectional view showing a portion of the filter assembly 210 according to an embodiment. FIG. 16 generally shows the same features depicted in FIG. 15 but at a different section of the filter assembly 210. In addition, FIG. 16 shows examples of gas venting flow paths VFP from the collection chamber 14, through the vent opening 218, the filter 216 and atmosphere openings 238 to the atmosphere.

Referring to FIGS. 15 and 16, in one embodiment, the carrier 214 and the base 212 may be connected to one another in a substantially gas-tight manner, such that gas vented from the collection chamber 14 through the vent opening 218 into the receptacle 222 may flow through the filter 216 to be deodorized before venting to the atmosphere. In some embodiments, the base 212 may optionally include a raised lip 234 projecting toward the filter 216. In one embodiment, the raised lip 234 may surround, or at least partially surround, the vent opening 218. In one embodiment, the raised lip 234 may be flush with the vent wall 232.

Figure 17:
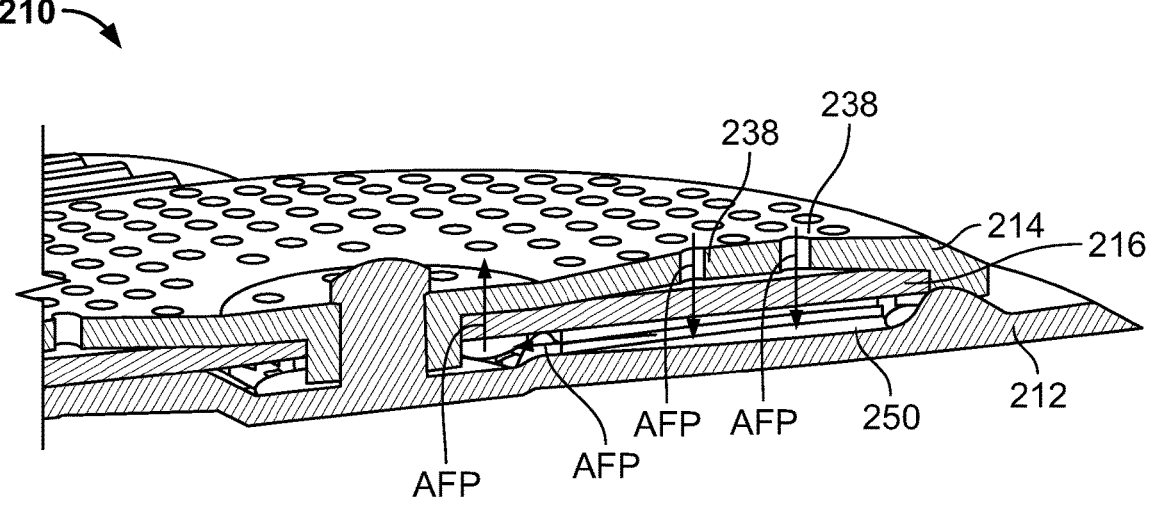
FIG. 17 is another perspective view showing a cross-section of a portion of the cleanable filter assembly of FIG. 9 according to an embodiment.

FIG. 17 is another perspective view showing a cross-section of a portion of the filter assembly 210 according to an embodiment. In one embodiment, in an area of the filter assembly 210 angularly spaced from the vent opening 218, air may flow along an airflow path AFP from the atmosphere through the atmosphere openings 238 of the carrier 214 and through the filter 216. The air may then flow through the one or more base channels 250, back through the filter 216 and exit to the atmosphere through atmosphere openings 238. Such airflow may dry and replenish functionality of the filter 216.

Accordingly, in the embodiments above, gas may be vented from the collection chamber 14 of the ostomy appliance 10 to the atmosphere through the filter assembly 210. For example, the gas may flow along the vent flow path VFP as shown in FIG. 16, from the collection chamber 14, into the vent opening 218 and through the filter 216. The gas may be deodorized in the filter 216 and exit to the atmosphere through the atmosphere vent openings 238 of the carrier 214.

In some instances, effluent from the collection chamber 14 may accumulate on the filter 216, for example, on the hydrophobic membrane of the filter 216, in the region of the vent opening 218. Such accumulation may occlude the filter 216 and restrict gas venting through the filter 216. According to the embodiments described above and shown in FIGS. 8-17. The carrier 214 and the filter 216, while secured to the base 212, may be rotated relative to the vent opening 218 to clean and/or refresh the filter 216. In this manner, accumulation of effluent on the filter 216 in or near the vent opening 218 may be removed from the vent opening 218 to improve gas venting.

Accordingly, the filter 216 may be rotated relative to the base 212 to clean and/or refresh the filter 216. For example, the filter 216 may be rotated relative to the base 212 by a user manipulating the carrier 214 with the handling tabs 248. The filter 216 may be rotated such that effluent accumulated on the filter 216 (or the hydrophobic membrane) in the vent opening 218 may be brought into contact with a portion of the base 212. For example, rotation of the filter 216 in a first direction may move the accumulated effluent into contact with the vent wall 232 and/or the raised lip 234. Further rotation of the filter 216 in the first direction may cause the accumulated effluent to be removed from the filter 216 by way of contact between the base 212 and the effluent. For example, the effluent may be scraped from the filter 216 by the vent wall 232 and/o the raised lip 234. In this manner, the filter 216 may be cleaned. In one embodiment, an angled or beveled vent wall may further promote removal of the accumulated effluent from the filter 216. In some embodiments, the filter 216 may then be rotated in a second direction, opposite to the first direction, so that a cleaned portion of the filter 216, i.e., a portion of the filter 216 from which effluent has been removed, is returned to extend over the vent opening 218 for gas venting.

Alternatively, or in addition, rotation of the filter 216 in the first direction may move a first portion of the filter 216 from a position extending across the vent opening 218 to a position adjacent to the vent opening 218 and move a second portion of the filter 216 to a position extending across the vent opening 218, for gas venting through the second portion. In some embodiments, accumulated effluent may be removed from the first portion during such rotation of the filter 216 to clean the first portion as described above. Alternatively, or in addition, in an embodiment, at least some accumulated effluent may move with the first portion of the filter 216 to a position adjacent to the vent opening 218, and a clean (i.e., non-occluded) second portion of the filter 216 may be moved to extend across the vent opening 218 for gas venting to refresh the filter 216.

In one embodiment, at least a portion of the filter 216 may be disposed in contact with at least a portion of the base 212. For example, the filter 216 may be disposed in sliding contact with a portion of the base 212 immediately adjacent the vent wall 232, and/or in sliding contact with the raised lip 234. The filter 216 may remain in sliding contact with the base 212 during rotation of the filter 216 relative to the base 212 to clean and/or refresh the filter 216. In other embodiments, the filter 216 may be positioned relative to the base 212 having a predetermined clearance. The predetermined clearance between the filter 216 and the base 212 may remain substantially constant during rotation of the filter 216 relative to the base 212. In one embodiment, accumulated effluent may be removed from the filter 216 by way of being moved into contact with a portion of the base 212 which contacts the filter 216. That is, a portion of the base 212, such as the vent wall 232 or raised lip 234 may act as a wiper to remove effluent from the filter 216.

In one embodiment, the filter 216 may be a single, continuous filter element, and the first and second portions of the filter 216 may be disposed at different locations along the filter element. In another embodiment, the filter 216 may include a plurality of filter elements. In one embodiment, first and second portions of the filter 216 may be included at respective filter elements.

Further, in some embodiments, the filter 116, 216 of the filter assembly 110, 210, may be removed and/or replaced. For example, the carrier 114, 214 may be removed from the base 112, 212. The filter 116, 216 retained by the carrier 114, 214 may be removed, and a new filter 116, 216 may be installed in the carrier 114, 214. The carrier 114, 214 may be reattached to the base 112, 212 for normal use. It will be appreciated that the filter 116, 216 may be cleaned after removal from the carrier 114, 214 and reused as well.

It is understood that the relative directions described above, e.g., "upward," "downward," "upper," "lower," "above," "below," are used for illustrative purposes only and may change depending on an orientation of the ostomy pouch and/or the patient. Accordingly, this terminology is non-limiting in nature. In addition, it is understood that one or more various features of an embodiment above may be used in, combined with, or replace other features of a different embodiment described herein.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

12

The invention claimed is:

1. An ostomy appliance comprising:
   a pouch wall defining at least a portion of a collection chamber configured to collect and store effluent from a stoma;
   an inlet formed in the pouch wall;
   a filter assembly connected to the pouch wall, the filter assembly comprising a base, a carrier, a fastening arrangement, and a filter, the base having a vent opening disposed in fluid communication with the collection chamber, the carrier movably connected to the base, the filter retained in the carrier, and the fastening arrangement slidably connects the carrier to the base,
   wherein the fastening arrangement allows linear sliding movement of the carrier and the filter relative to the base in a first linear sliding direction and a second linear sliding direction opposite to the first linear sliding direction, and prevents movement of the carrier and the filter relative to the base in a third direction that extends at a non-parallel angle relative to the first sliding direction and the second sliding direction, and
   wherein the base comprises a plate and a flange extending from the plate, the flange comprises an elongated closed loop, and the carrier is contained interior of the closed loop and connected to the flange for sliding movement.

2. The ostomy appliance of claim 1, wherein the filter is disposed in sliding contact with the base during movement of the filter relative to the vent opening.

3. The ostomy appliance of claim 1, wherein the filter includes a first portion extending across the vent opening and a second portion adjacent to the vent opening.

4. The ostomy appliance of claim 3, wherein movement of the filter relative to the vent opening in a first direction causes the first portion to move away from the vent opening and the second portion to extend across the vent opening.

5. The ostomy appliance of claim 4, wherein movement of the second portion to extend across the vent opening is configured to refresh the filter.

6. The ostomy appliance of claim 4, wherein movement of the filter relative to the vent opening in a second direction opposite to the first direction causes the first portion to move to a position extending across the vent opening and the second portion to move away from the vent opening.

7. The ostomy appliance of claim 1, wherein the carrier comprises a receptacle and the filter is retained in the receptacle.

8. The ostomy appliance of claim 7, wherein the carrier comprises two receptacles and the filter includes first and second filter elements retained in respective receptacles.

9. The ostomy appliance of claim 1, wherein the filter is disposed between the carrier and the base.

10. The ostomy appliance of claim 1, wherein the carrier comprises a plurality of atmosphere vent openings for venting gas from the collection chamber to the atmosphere.

11. The ostomy appliance of claim 1, wherein the filter comprises a hydrophobic membrane.

12. The ostomy appliance of claim 1, wherein the linear sliding movement of the carrier and the filter and causes linear movement of the filter relative to the vent opening to clean or refresh the filter.

13. The ostomy appliance of claim 12, wherein the linear sliding movement of the carrier is along a major axis of the elongated closed loop.

14. The ostomy appliance of claim 13, wherein linear sliding movement of the carrier moves the carrier relative to the base from a configuration in which a first end of the carrier is proximate a first end of the elongated closed loop and a second end of the carrier is separated from a second end of the elongated closed loop, wherein the first end of the elongated closed loop and the second end of the elongated closed loop are separated along the major axis.

15. The ostomy appliance of claim 1, wherein the movement of the filter relative to the base is configured to clean the filter by bringing accumulated effluent on the filter into contact with the base to remove the accumulated effluent from the filter.

16. The ostomy appliance of claim 15, wherein the base comprises a vent wall around the vent opening, and the vent wall removes the accumulated effluent from the filter in response to movement of the filter relative to the base.

17. The ostomy appliance of claim 15, wherein the base comprises a raised lip, and the raised lip removes the accumulated effluent from the filter in response to movement of the filter relative to the base.

18. The ostomy appliance of claim 1, wherein the base comprises a raised lip, and the filter is disposed in sliding contact with the raised lip.

19. The ostomy appliance of claim 1, wherein the filter is removably retained in the carrier.

20. An ostomy appliance comprising:

a pouch wall defining at least a portion of a collection chamber configured to collect and store effluent from a stoma;

an inlet formed in the pouch wall; and a slidable filter assembly connected to the pouch wall, the slidable filter assembly comprising a base, a carrier, a fastening arrangement that slidably connects the carrier with the base, and a filter in slidable contact with the base and movable with the carrier relative to the base, the base having a vent opening disposed in fluid communication with the collection chamber, wherein the fastening arrangement allows linear sliding movement of the carrier and the filter relative to the base in a first linear sliding direction and a second linear sliding direction opposite to the first sliding direction, and prevents movement of the carrier and the filter relative to the base in a third direction that extends at a non-parallel angle relative to the first sliding direction and the second sliding direction, and wherein the base comprises a plate and a flange extending from the plate, the flange comprises an elongated closed loop, and the carrier is contained interior of the closed loop and connected to the flange for sliding movement.

21. The ostomy appliance of claim 20, wherein the base further comprises a raised lip and the filter is disposed in sliding contact with the raised lip.

*   *   *   *   *